United States Patent [19]

Kao

[11] Patent Number: 4,906,103

[45] Date of Patent: Mar. 6, 1990

[54] DEVICES AND METHODS FOR PREPARING A SOLUTION FOR MEDICINAL PURPOSES

[76] Inventor: Ti Kao, P.O. Box 14, Rego Park, N.Y. 11374-0014

[21] Appl. No.: 85,515

[22] Filed: Aug. 13, 1987

Related U.S. Application Data

[63] Continuation of Ser. No. 615,124, May 30, 1984, abandoned, and a continuation of Ser. No. 849,392, Apr. 7, 1986, abandoned.

[51] Int. Cl.[4] .................... B01F 13/00; B65D 25/08; B65D 33/00; A61M 5/00

[52] U.S. Cl. .................... 366/130; 141/313; 206/219; 222/95; 604/404; 604/416

[58] Field of Search .............. 366/130, 184, 189, 191; 206/219, 620, 221, 222; 604/262, 406, 410, 416, 404; 222/373, 401, 394, 541, 105, 95; 141/382, 114, 313, 100, 102, 105, 106, 113, 311 R, 319, 383, 98, 2, 10, 1, 9; 210/416.1, 257.1, 257.2; 53/428, 431, 434, 469, 473, 474, 111 R, 512; 116/206

[56] References Cited

U.S. PATENT DOCUMENTS

| | | | |
|---|---|---|---|
| 2,879,207 | 3/1959 | Poitras | 604/406 X |
| 3,950,158 | 4/1976 | Gossett | 206/219 X |
| 4,090,514 | 5/1978 | Hinck et al. | 222/95 X |
| 4,147,278 | 4/1979 | Uhlig | 222/95 X |
| 4,226,330 | 10/1980 | Butler | 206/620 |
| 4,265,760 | 5/1981 | Abel et al. | 604/410 X |
| 4,282,863 | 8/1981 | Beigler et al. | 206/219 X |
| 4,372,100 | 2/1983 | Miller et al. | 141/105 X |
| 4,430,078 | 2/1984 | Sprague | 222/95 X |
| 4,507,116 | 3/1985 | Leibinsohn | 222/95 X |
| 4,610,684 | 9/1986 | Knox et al. | 604/416 |

FOREIGN PATENT DOCUMENTS 0040427 11/1981 European Pat. Off. ............ 604/406

OTHER PUBLICATIONS

Avis et al, "Sterile Preparation for the Hospital Pharmacist", Ann Arbor Science ©1982.

*Primary Examiner*—Harvey C. Hornsby
*Assistant Examiner*—Scott J. Haugland
*Attorney, Agent, or Firm*—Lathrop & Clark

[57] ABSTRACT

A device for the preparation of sterile pharmaceutical solutions for intravenous use includes a first bag (1), a second bag (8), and a filtration unit (5). The filtration unit (5) has an inlet tube and an outlet tube, the inlet tube of the filtration unit (5) being attached to an outlet port in the first bag (1) and the outlet tube being connected to an inlet port through which aqueous solvent may be introduced. The first bag (1) has a flexible lining that defines a chamber and a plurality of individual storage containers (3) attached to the lining of the chamber. The containers (3) have tops that may be snapped off by manipulation of the lining opposite the chamber. The removal of the container allows ingredients contained within to be individually released into the chamber on demand. The combination of the ingredients and the aqueous solvent forms a pharmaceutical solution of known composition. The first bag (1) may be placed within an enclosure into which air is pumped to exert a positive pressure upon the first bag (1) to force the pharmaceutical solution through the filtration unit (5) and into the second bag (8). The second bag (8) may also have individual storage containers (9) that contain sterile medicinal preparations that may be released into the pharmaceutical solution.

19 Claims, 3 Drawing Sheets

DEVICES AND METHODS FOR PREPARING A SOLUTION FOR MEDICINAL PURPOSES

This application is a continuation of previous applications submitted 5/30/84, Ser. No. 615,124, abandoned, Gp. No. 242, patent examiner A. Dahlberg and application filed on 4/07/86, Ser. No. 06/849,392, abandoned, examiner S. Haugland, Art Unit 242.

PERTINENT REFERENCES

U.S. Patent Documents

| | | | |
|---|---|---|---|
| 4282863 | 8/1981 | Beigler et al | 206/219X |
| 4226330 | 10/1980 | Butler | 206/219X |
| 1332985 | 3/1920 | Jarrett | 366/130X |
| 3764796 | 10/1973 | Gilliam et al | 222/541X |
| 4215628 | 8/1980 | Dodd, Jr. | 99/323 |
| 2787269 | 4/1957 | Cohen | 206/219X |
| 4511533 | 4/1985 | Guadagno et al | 206/219X |
| 4609369 | 9/1986 | Ball | 206/219X |
| 4364474 | 12/1982 | Hollander, Jr | 366/130X |
| 4522622 | 6/1985 | Peery et al | 604/410X |

BACKGROUND OF THE INVENTION

1. Field of the Invention

The present invention relates to a portable device for the preparation of and intravenous delivery of sterilized nutrients or medicinal solutions for use in patients who, for one reason or another, are unable to eat or accept nutrients or medicines by mouth. The device will be used under conditions in which Total Parenteral Nutrition (TPN) is indicated or where the administration of drugs, electrolytes or nutrients cannot be taken by mouth.

2. Brief Description of Prior Arts

The existing method and device by Biegler et al (Aug. 11, 1981, U.S. Pat. No. 4,282,863) invented for the preparation of sterile solutions of nutrients from dry ingredients for intravenous use relies heavily on gravity filtration of the solutions through a 0.22 micron bacteria filter. Their method and device proposes that the nutrient composition (i.e. concentration) of the final solution must be capable of passing through the filter within a 2 hour test period, if not, the nutrient composition of the solution is not preferred by their method and device (re: column 3, lines 8 to 20; column 5, lines 36 to 44). In support of his patent, Beigler et al provide data that hot water (185° F.) solutions containing 25% dextrose or one containing 4.5% of an amino acid mixture meet the 2 hour filtration test. It should be pointed out that since heat is known to decrease the viscosity of fluids and of concentrated solutions thereby favoring increased filtration rates, the data provided are not applicable to the solutions of nutrients which would normally be prepared at ambient or room temperature (i.e. 70° F.). Nutrient solutions commonly required in TPN therapy can vary greatly in concentration (e.g. amino acid mixtures can approach 11.4%, dextrose may vary from 5 to 35% and other preparations may reach as high as 40%). Since the viscosity of solutions, in general, increases with concentration and since flow rate through a filter is inversely proportional to viscosity (i.e. low filtration rates with high viscosity; high filtration rates with low viscosity), the gravity filtration method of preparing sterile nutrient solutions proposed by Beigler et al is too slow, time consuming and unacceptable for the wide variety and range of nutrient requirements needed for TPN therapy. Furthermore, lengthy filtration times associated with gravity filtration of concentrated solutions used in TPN therapy may contribute to the growth and release of pyrogens from bacteria which may be present in the solutions and become trapped within the bacterial filter.

To overcome the major problem of slow filtration rates associated with the gravity filtration of nutrient solutions through a fine bacterial filter (0.20 micron), we have developed an Intravenous Delivery System consisting of two (2) compartments (Part 1: Storage/-Mixing Chamber; Part 2: Receptacle/Delivery chamber) joined by an in-line filter unit which includes a coarse 5 micron and fine 0.20 micron bacteria filter. Since it is well known that the passage of solutions of varying concentrations through varying type filters are greatly increased by the application or removal of air pressure, this system also includes a separate air pressurizing device which when applied to the Storage/Mixing chamber containing the appropriate dissolved nutrients or medicinal substances will greatly increase the filtration rate making the sterile filtrate appearing in the Receptacle/Delivery chamber readily available for intravenous use in patients.

SUMMARY OF THE INVENTION

This invention relates to a two compartment system (Storage/Mixing chamber and Receptacle/Delivery chamber) composed of two polymeric plastic IV bags or containers joined by an in-line filtration unit (containing a coarse 5 micron and fine 0.20 micron filters) to be used for the rapid preparation of sterile solutions of nutrients, electrolytes, vitamins and other medicinal required for Total Parenteral Nutrition (TPN) therapy or intravenous administration to man or other mammals. The first compartment hereby referred to as the Storage/Mixing chamber is designed to include within the chamber the attachment of small "snap-top" containers (plastic in composition) for storage of dry or liquid ingredients (nutrients, electrolytes, buffering agents, vitamin, medicinals), the contents of which can be released on demand into the chamber for the production of a known pharmaceutical preparation. Sterile pyrogen free water for the purpose of making the solution can be introduced into the Storage/Mixing chamber through an inlet port provided. The in-line filtration unit separates the Storage/Mixing chamber from the Receptacle/Delivery chamber and contains a coarse (5 micron) and fine (0.20 micron) filter for the entrapment of particulate matter and bacteria respectively. To hasten filtration, the solution in the Storage/Mixing chamber is placed in a device where positive air pressure (10 to 75 psi) can be exerted on the chamber. The air pressure device is constructed of two parts held together with a set of hinges on one side and locking devices on the opposing side. It is fabricated of durable "see-thru" plastic and is equipped with a threaded fitting to accommodate an air pump and air pressure meter to monitor air pressure. Air pressure in the device is developed by using an air pump similar to that found on conventional stethoscopes. Under positive air pressure the solution in the Storage/Mixing chamber undergoes rapid filtration and appears as a sterile solution in the Receptacle/-Delivery chamber. After all of the contents of the Storage/Mixing chamber have filtered into the Receptacle/Delivery chamber, air pressure in the device is released (via 2-way air valve on air pump), the filtration inlet tubing just above the Receptacle/Delivery chamber is clamped off and cut above the clamp leaving the Receptacle/Delivery chamber available for immediate intravenous use. The Receptacle/Delivery chamber may also be equipped with containers ("snap-top" as described above), attached within the chamber, for containment of sterile pharmaceuticals in liquid form (e.g. insulin, glucagon, etc.) which may be released on demand for addition to the sterile pharmaceutical preparation within the Receptacle/Delivery chamber.

This Intravenous Delivery System for the preparation and delivery of sterile pharmaceuticals offers several advantages which include, (a) the rapid production of solutions from dry pharmaceutical preparations and their sterilization by pressure filtration: a procedure applicable to concentrated solutions of amino acid mixtures and dextrose employed for Total Parenteral Nutrition (TPN) therapy or intravenous use. Sterilization by gravity filtration through a 0.2 micron bacteria filter of pharmaceutical solutions required for TPN therapy is too slow and in many instances unattainable, (b) the preparation of pharmaceuticals on demand from dry powders is not only cost effective from the standpoint of reducing the transportation costs associated with prepackaged bulk pharmaceutical solutions but also overcomes the problem of instability of solutions upon storage, (c) since it is a portable device, it can be utilized under conditions where medical facilities are not available, and (d) the system with its numerous containers for the containment of pharmaceuticals makes it a highly versatile unit for the treatment of numerous disorders.

DETAILED DESCRIPTION OF THE PREFERRED EMBODIMENTS OF THE INVENTION

Figure 1:
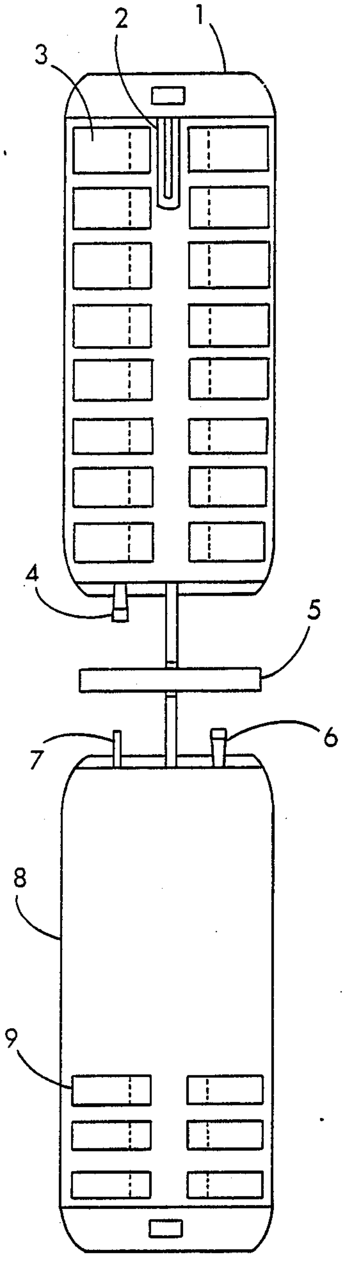
FIG. 1. Illustrates a plane view of the Intravenous Delivery System for Total Parenteral Nutrition (TPN) or intravenous administration of medicinals.

The Intravenous Delivery System (FIG. 1) invented includes two modified conventional intravenous plastic bags (FIG. 1, item 1, 8) joined by an in-line filtration unit (FIG. 1, item 5). One bag hereby referred to as a Storage/Mixing chamber (FIG. 1, item 1), is fitted with individual storage containers (FIG. 1, item 3) attached within the chamber, for the containment of dry or liquid ingredients that are commonly used for Total Parenteral Nutrition (TPN) or intravenous use. These ingredients, which meet all USP standards for purity and sterility, may include amino acid mixtures, dextrose, electrolytes, vitamins or other medicinals. The containers within the chamber are packaged to have snap-off tops such that the ingredients within the containers can be released into the chamber on demand. The ingredients released into the chamber can be solubilized into aqueous solutions by the introduction of sterile pyrogen free water or other suitable USP solution through the inlet port (FIG. 1, item 4) of the chamber. After introduction of the aqueous solvent the chamber (bag) can be kneaded to facilitate the mixing and solubilization of the ingredients. Solutions of amino acid mixtures often require adjustment of final pH before intravenous administration. To insure that the pH of the final solution in the Storage/Mixing chamber meets USP requirements for pH, buffering agents when needed are added to the dry or liquid ingredients when they are packaged in the storage containers. A pH metering device (FIG. 1, item 2) is also included in the Storage/Mixing chamber as a check on the final pH.

Figure 2:
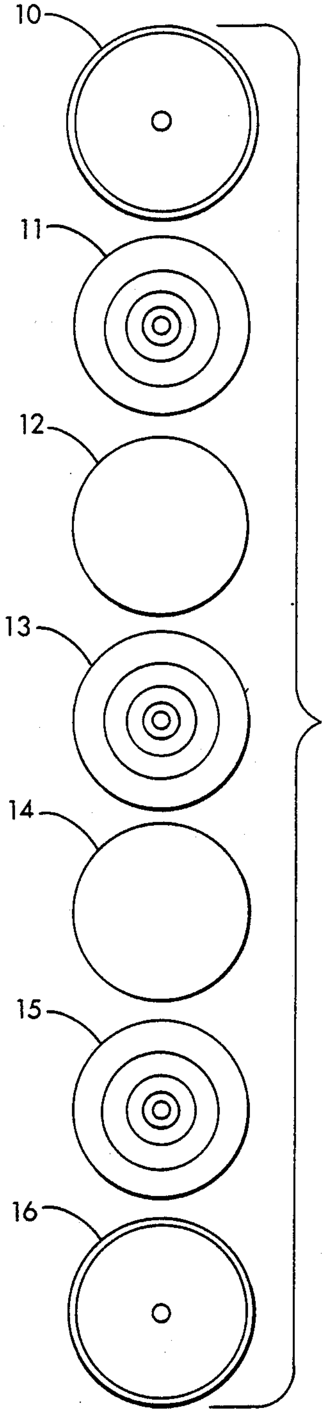
FIG. 2. Illustrates the in-line filtration unit and its structural components.

The in-line filtration unit (FIG. 1, item 5; FIG. 2) joins the Storage/Mixing chamber (bag) (FIG. 1, item 1) to the Receptacle/Delivery chamber (bag) (FIG. 1, item 8). The outlet from the Storage/Mixing chamber into the filtration unit is heat sealed as to form a bond that can sustain a positive pressure (0 to 75 psi) to be imposed on the solutions in the Storage/Mixing chamber. The filtration unit consists of a coarse 5 micron filter (FIG. 2, item 12) for particulate matter and a fine 0.20 micron filter (FIG. 2, item 14) for bacteria. Polysulfone or polycarbonate filter membranes come in a variety of pore sizes (0.2, 0.45 and 5 micron) and can operate at a maximum air pressure of 60 psi. These filters are currently available from commercial vendors (millipore Corp., Gelman Sciences, Inc.). As an example and in support of the rapid filtration rates attainable with these filters when exposed to positive air pressure, we cite the Acrocap (trade name) filter unit which is manufactured by Gelman Sciences, Inc., Ann Arbor, Mich. This sterile, non-pyrogenic filter unit contains a 0.20 micron Supor 200 polysulfone membrane. It is ideally suited for the rapid filtration and sterilization of aqueous salt solutions ranging in volume from 500 ml to 3000 ml. Two hundred (200) milliliters per minute is the typical flow rate of a serum free tissue culture media through the membrane with a surface area of 15 $cm^2$ and a positive air pressure of 10 to 20 psi. In our filtration unit the filtration membranes are separated and supported by a plastic matrix (FIG. 2, items 10, 11,13,15,16).

The Receptacle/Delivery chamber (FIG. 1, item 8) is the receiving chamber for the sterile filtrate which occurs after the contents of the solution in the Storage/-Mixing chamber (FIG. 1, itme 1) has been subjected to positive air pressure. This chamber may also be equipped with containers (FIG. 1, item 9) attached to the inside of the chamber for the containment of sterile liquid pharmaceuticals which can be released and added to the contents of the chamber directly. This is particularly desirable for medicinal agents like insulin and other protein preparations which are known to bind to foreign surfaces. Filtration of these agents would result otherwise in considerable loss of active principal. After filtration is complete, i.e. all the contents of the Storage/Mixing chamber have appeared in the Receptacle/-

Figure 10:
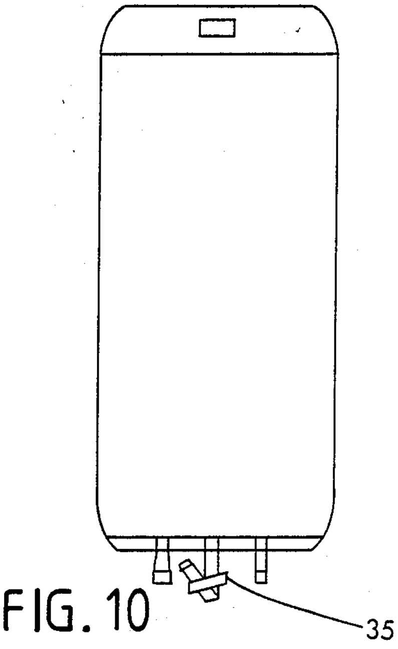
FIG. 10. Plane view of Receptacle/Delivery chamber after filtration is complete. Note the filtration tube into the chamber has been cut off and clamped freeing the chamber for immediate TPN or intravenous use.
Figure 11:
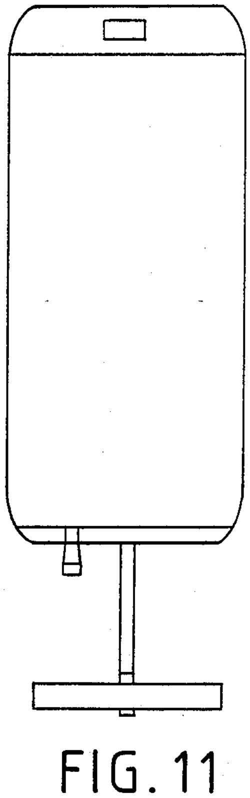
FIG. 11. Plane view of an empty Storage/Mixing chamber.

Delivery chamber, the inlet tube into the Receptacle/-Delivery chamber is clamped off (FIG. 10, item 35) with the clamp provided and the tubing cut above the clamp releasing the Receptacle/Delivery chamber for immediate intravenous use to the patient. An outlet port (FIG. 1, item 7) is provided for the attachment of an intravenous unit (drip chamber) for connection to the patient's vein.

Figure 3:
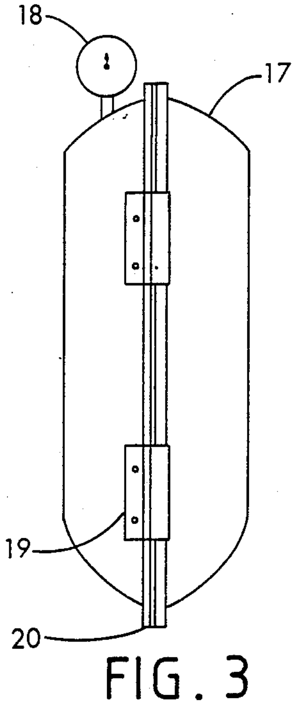
FIGS. 3 and 4: Illustrates opposing side views of air pressurization device and its components.
Figure 4:
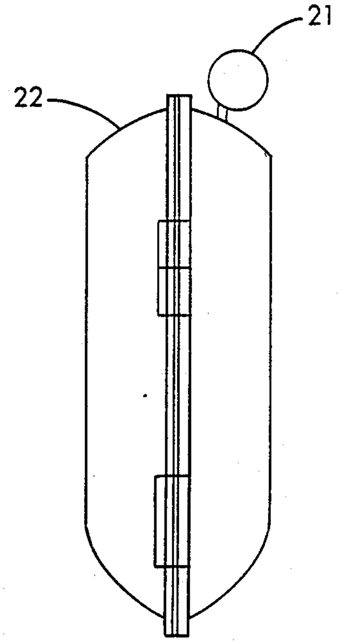
Figure 5:
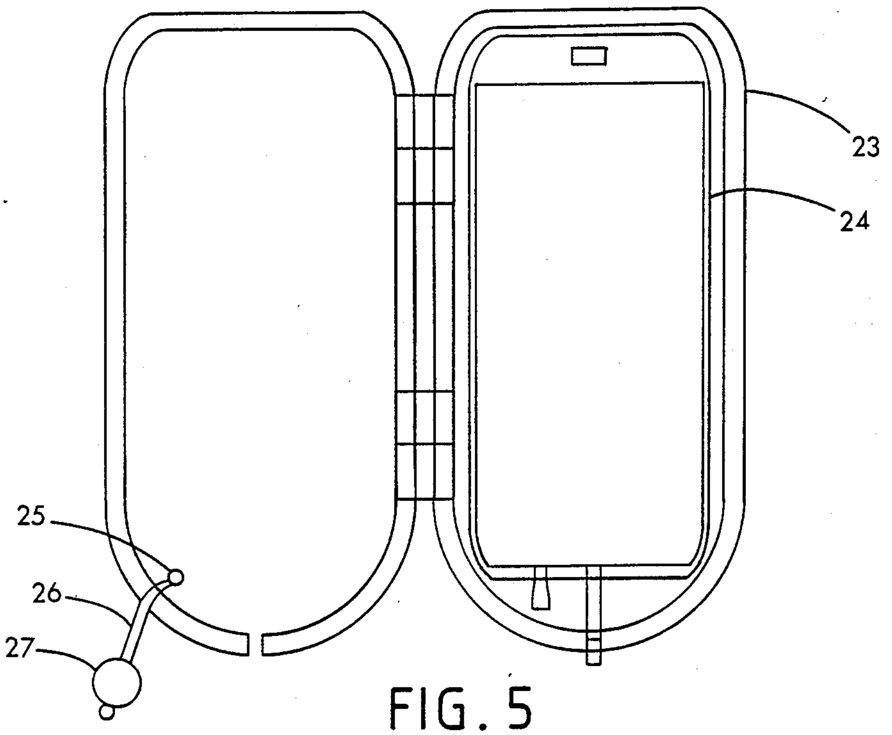
FIG. 5. Illustrates the air pressurization device in the open position with the Storage/Mixing chamber resting on the inside of one-half of the device. Each of the bags has a capacity between 250 and 1000 ml.
Figure 7:
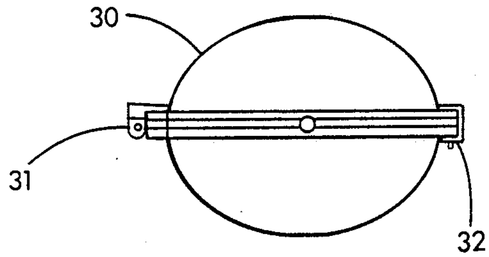
FIG. 7. Top view of the air pressurization device.
Figure 6:
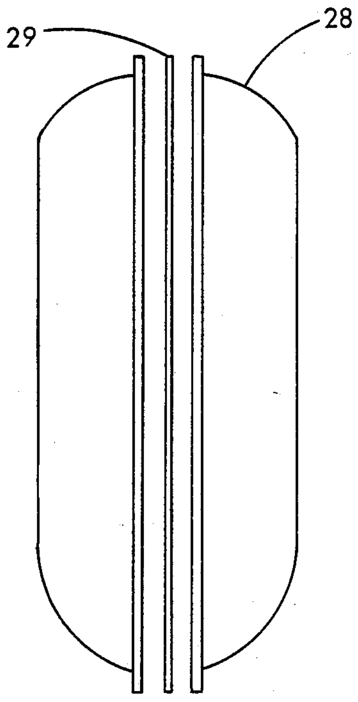
FIG. 6. A side view of air pressure device showing the air-seal gasket.
Figure 8:
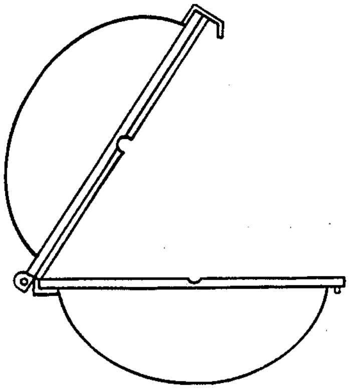
FIG. 8. Top view of the air pressurization device showing the unit in an open position.
Figure 9:
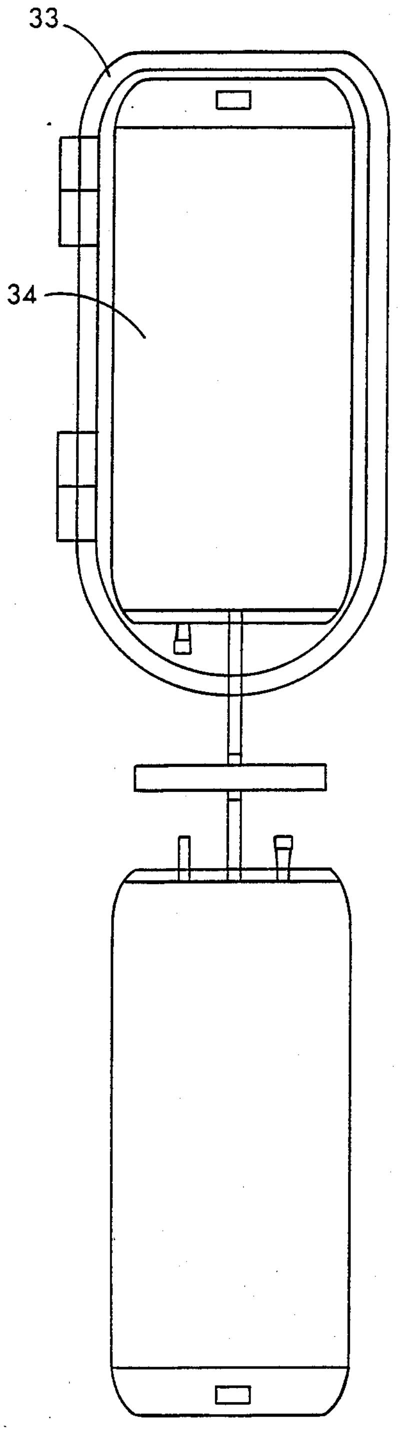
FIG. 9. Plane view of air pressurization device fitted over the Storage/Mixing chamber.

The air pressure device (FIGS. 4 thru 8) shown is structured of acrylic plastic or a similar see-thru plastic material. It consists of two parts held together with 2 brass or stainless steel hinges (FIG. 7, item 31) and an appropriate locking device on the opposing side (FIG. 7, item 32). A rubber or neoprene gasket (FIG. 6, item 29) is fitted to the inside outer rim of the device such that when in the closed position (locked) an air tight seal is formed. The dimensions of the unit are such as to completely enclose the Storage/Mixing chamber (FIGS. 5 and 9). There is an opening on the device which allows it to clamp into the inlet of the filtration unit. The device is fitted with a conventional air pressure meter (FIG. 3, item 18, FIG. 4, item 21) and a threaded inlet fitting (FIG. 5, item 25) to accommodate a hand operated air pump (FIG. 5, item 26,27) with a two way valve for air intake and release and capable of developing air pressure within the chamber of at least 75 psi. This device is self contained and can be used repeatedly whenever air pressurization filtration of the Storage/Mixing chambers are needed.

EXAMPLE 1

Pharmaceutical preparations now in common use in TPN therapy

Aminosyn (Abbott Labs) preparations contain 8.5 % amino acid mixtures with and without electrolytes. 10% is also available with select electrolytes. The amino acid mixtures consist of 8 essential and 8 non-esstential amino acids. Electrolytes when indicated include sodium, potassium, magnesium, chloride, acetate and phosphate.

As opposed to the prepackaged prepared solutions above, our invention allows the placement of the essential amino acids to be placed in one capsule, the non-essential amino acids can be placed in another capsule and electrolytes separately included in another capsule. In powder form the bag and capsules will weigh a fraction of the final prepackaged solution.

EXAMPLE 2

Prepackaged Dextrose solutions are available for TPN or IV use in the following concentrations: 10%, 20%, 30%, 40%, 50 %, 60%, and 70%. Varying amounts of dry dextrose can be placed in the individual capsules attached to the Storage/Mixing chamber to make any desired solution either alone or in combination with amino acid mixtures, or other additives required.

What is claimed:

1. A device for the preparation of sterile pharmaceutical solutions for subsequent intravenous use in man or mammals, comprising:

(a) a first bag having a flexible lining that defines a chamber, an inlet port leading to the chamber and an outlet port leading from the chamber, and a plurality of containers attached to the lining of the chamber, the inlet port receiving aqueous solvent and the containers containing ingredients that are individually releasable into the chamber, the ingredients being a solute that forms a pharmaceutical solution of known composition with the aqueous solvent;

(b) a filtration unit having an inlet tube and an outlet tube, the inlet tube of the filtration unit being attached to the outlet port of the first bag;

(c) a second bag having an inlet port and an outlet port, the inlet port of the second bag being attached to the outlet tube of the filtration unit, and the outlet port being attachable to an intravenous unit; and (d) means for exerting a positive pressure upon the chamber of the first bag to force the pharmaceutical solution from the first bag through the filtration unit and into the second bag.

2. The device of claim 1 wherein the filtration unit comprises a coarse filter membrane of a size suitable for the filtration of particulate matter and a fine filter membrane of a size suitable for the filtration of bacteria.

3. The device of claim 2 wherein the coarse filter membrane is a filter of approximately 5 microns.

4. The device of claim 2 wherein the fine filter membrane is a filter of approximately 0.20 microns.

5. The device of claim 1 wherein the means for exerting a positive pressure is an enclosure which surrounds the first bag and includes an inlet through which air is pumped.

6. The device of claim 5 wherein the enclosure is transparent.

7. A device for the preparation of sterile pharmaceutical solutions for subsequent intravenous use in man or mammals, comprising:

(a) a first bag having a flexible lining that defines a chamber, an inlet port leading to the chamber and an outlet port leading from the chamber, and a container attached to the lining of the chamber, the inlet port receiving aqueous solvent and the container containing ingredients that are releasable into the chamber, the ingredients being a solute that forms a pharmaceutical solution of known composition with the aqueous solvent;

(b) a filtration unit having an inlet tube and an outlet tube, the inlet tube of the filtration unit being attached to the outlet port of the first bag;

(c) a second bag having an inlet port and an outlet port, the inlet port of the second bag being attached to the outlet tube of the filtration unit, and the outlet port being attachable to an intravenous unit; and (d) an enclosure which surrounds the first bag and includes an inlet through which air is pumped to exert a positive pressure upon the chamber of the first bag to force the pharmaceutical solution from the first bag through the filtration unit and into the second bag and wherein the enclosure has hinges to open the enclosure into two halves which can be closed about the first bag, the enclosure having a gasket between the halves to provide an air-tight seal.

8. The device of claim 1 wherein the containers include means for releasing the ingredients from the side of the lining opposing the chamber.

9. The device of claim 8 wherein the means for releasing ingredients is a top that may be snapped off of each of the containers to release the ingredients, the top being manipulable from the side of the lining opposing the chamber.

10. A device for the preparation of sterile pharmaceutical solutions for subsequent intravenous use in man or mammals, comprising:

(a) a first bag having a flexible lining that defines a chamber, an inlet port leading to the chamber and an outlet port leading from the chamber, and a container attached to the lining of the chamber, the inlet port receiving aqueous solvent and the container containing ingredients that are releasable into the chamber, the ingredients being a solute that forms a pharmaceutical solution of known composition with the aqueous solvent;

(b) a filtration unit having an inlet tube and an outlet tube, the inlet tube of the filtration unit being attached to the outlet port of the first bag;

(c) a second bag having an inlet port and an outlet port, the inlet port of the second bag being attached to the outlet tube of the filtration unit, and the outlet port being attachable to an intravenous unit, wherein the second bag has a lining that defines a chamber, and a container that contains ingredients that are releasable into the second bag; and (d) means for exerting a positive pressure upon the chamber of the first bag to force the pharmaceutical solution from the first bag through the filtration unit and into the second bag.

11. The device of claim 10 wherein the container of the second bag includes means for releasing the ingredients into the second bag from the side of the lining opposing the chamber.

12. The device of claim 11 wherein the means for releasing the ingredients into the second bag is a top that may be snapped off of the container of the second bag to release the ingredients into the second bag, the top being manipulable from the side of the lining opposing the chamber.

13. The device of claim 1 wherein the outlet tube of the filtration unit is flexible in order that the outlet tube may be clamped off and severed upon completion of the transfer of the solution from the first bag to the second bag, thus forming an independent and portable second bag.

14. The device of claim 1 wherein the capacity of each of the two bags is between 250 and 1,000 ml in capacity.

15. The device of claim 1 wherein the bags are made of polymeric plastic.

16. The device of claim 1 wherein the ingredients contained within the container are selected from the group consisting of amino acids, vitamins, dextrose, and electrolytes.

17. The device of claim 10 wherein the ingredients within the container of the second bag are proteins.

18. The device of claim 1 wherein the ingredients within the container in the second bag are sterile medicinal preparations which do not require filtration.

19. A device for the preparation of sterile pharmaceutical solutions for subsequent intravenous use in man or mammals, comprising:

(a) a first bag having a flexible lining that defines a chamber, an inlet port leading to the chamber and an outlet port leading from the chamber, and a container attached to the lining of the chamber, the inlet port receiving aqueous solvent and the container containing ingredients that are releasable into the chamber, the ingredients being a solute that forms a pharmaceutical solution of known composition with the aqueous solvent;

(b) a filtration unit having an inlet tube and an outlet tube, the inlet tube of the filtration unit being attached to the outlet port of the first bag;

(c) a second bag having an inlet port and an outlet port, the inlet port of the second bag being attached to the outlet tube of the filtration unit, and the outlet port being attachable to an intravenous unit, (d) means for exerting a positive pressure upon the chamber of the first bag to force the pharmaceutical solution from the first bag through the filtration unit and into the second bag; and (e) a pH meter contained within the first bag.

* * * * *